United States Patent
Pandev et al.

(10) Patent No.: US 10,139,352 B2
(45) Date of Patent: Nov. 27, 2018

(54) MEASUREMENT OF SMALL BOX SIZE TARGETS

(71) Applicant: KLA-Tencor Corporation, Milpitas, CA (US)

(72) Inventors: Stilian Ivanov Pandev, Santa Clara, CA (US); Wei Lu, San Jose, CA (US); Andrei V. Shchegrov, Campbell, CA (US); Pablo Rovira, Santa Clara, CA (US); Jonathan M. Madsen, Los Altos, CA (US)

(73) Assignee: KLA-Tenor Corporation, Milpitas, CA (US)

( * ) Notice: Subject to any disclaimer, the term of this patent is extended or adjusted under 35 U.S.C. 154(b) by 317 days.

(21) Appl. No.: 14/882,370

(22) Filed: Oct. 13, 2015

(65) Prior Publication Data

US 2016/0109375 A1    Apr. 21, 2016

Related U.S. Application Data

(60) Provisional application No. 62/065,662, filed on Oct. 18, 2014.

(51) Int. Cl.
*G01N 21/93* (2006.01)
*G01N 21/956* (2006.01)

(52) U.S. Cl.
CPC .......... *G01N 21/956* (2013.01); *G01N 21/93* (2013.01)

(58) Field of Classification Search
CPC .......................... G01N 21/956; G01N 21/93
See application file for complete search history.

(56) References Cited

U.S. PATENT DOCUMENTS

| | | |
|---|---|---|
| 5,608,526 A | 3/1997 | Piwonka-Corle et al. |
| 5,859,424 A | 1/1999 | Norton et al. |
| 6,429,943 B1 | 8/2002 | Opsal et al. |
| 6,633,831 B2 | 10/2003 | Nikoonahad et al. |
| 6,734,967 B1 | 5/2004 | Piwonka-Corle et al. |
| 6,816,570 B2 | 10/2004 | Janik et al. |
| 6,895,075 B2 | 5/2005 | Yokhin et al. |
| 6,972,852 B2 | 12/2005 | Opsal et al. |
| 7,478,019 B2 | 1/2009 | Zangooie et al. |
| 7,826,071 B2 | 11/2010 | Shchegrov et al. |
| 7,929,667 B1 | 4/2011 | Zhuang et al. |

(Continued)

*Primary Examiner* — Kyoung Lee
(74) *Attorney, Agent, or Firm* — Spano Law Group; Joseph S. Spano (57) ABSTRACT

Methods and systems for measuring metrology targets smaller than the illumination spot size employed to perform the measurement are described herein. Collected measurement signals contaminated with information from structures surrounding the target area are reconstructed to eliminate the contamination. In some examples, measurement signals associated one or more small targets and one or more large targets located in close proximity to one another are used to train a signal reconstruction model. The model is subsequently used to reconstruct measurement signals from other small targets. In some other examples, multiple measurements of a small target at different locations within the target are de-convoluted to estimate target area intensity. Reconstructed measurement signals are determined by a convolution of the illumination spot profile and the target area intensity. In a further aspect, the reconstructed signals are used to estimate values of parameters of interest associated with the measured structures.

20 Claims, 7 Drawing Sheets

(56) References Cited

U.S. PATENT DOCUMENTS

| | | |
|---|---|---|
| 7,933,026 B2 | 4/2011 | Opsal et al. |
| 2013/0114085 A1 | 5/2013 | Wang et al. |
| 2014/0111791 A1 | 4/2014 | Manassen et al. |
| 2014/0172394 A1 | 6/2014 | Kuznetsov et al. |
| 2014/0222380 A1 | 8/2014 | Kuznetsov et al. |
| 2014/0297211 A1 | 10/2014 | Pandev et al. |
| 2014/0316730 A1 | 10/2014 | Shchegrov et al. |
| 2015/0042984 A1 | 2/2015 | Pandev et al. |
| 2015/0046118 A1 | 2/2015 | Pandev et al. |

$$140 \begin{bmatrix} {}^1S_{L,1} \\ {}^2S_{L,1} \\ \vdots \\ {}^MS_{L,1} \end{bmatrix} \quad \begin{bmatrix} {}^1S_{S,1} \\ {}^2S_{S,1} \\ \vdots \\ {}^US_{S,1} \end{bmatrix} 141$$

MEASUREMENT OF SMALL BOX SIZE TARGETS

CROSS REFERENCE TO RELATED APPLICATION

The present application for patent claims priority under 35 U.S.C. § 119 from U.S. provisional patent application Ser. No. 62/065,662, entitled "Method for Measuring Small Box Size Targets," filed Oct. 18, 2014, the subject matter of which is incorporated herein by reference in its entirety.

TECHNICAL FIELD

The described embodiments relate to metrology systems and methods, and more particularly to methods and systems for improved parameter measurement.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

A lithographic process, as described above, is performed to selectively remove portions of a resist material overlaying the surface of a wafer, thereby exposing underlying areas of the specimen on which the resist is formed for selective processing such as etching, material deposition, implantation, and the like. Therefore, in many instances, the performance of the lithography process largely determines the characteristics (e.g., dimensions) of the structures formed on the specimen. Consequently, the trend in lithography is to design systems and components (e.g., resist materials) that are capable of forming patterns having ever smaller dimensions.

Inspection processes based on optical metrology are used at various steps during a semiconductor manufacturing process to detect defects on wafers to promote higher yield. Optical metrology techniques offer the potential for high throughput without the risk of sample destruction. A number of optical metrology based techniques including scatterometry implementations and associated analysis algorithms to characterize device geometry have been described. However, it remains a challenge to reduce the measurement box size.

A small measurement box size is especially important in semiconductor inline product metrology where the area available for metrology targets is minimal. The need to reduce the size of metrology targets is becoming more important as multiple metrology targets are being introduced across the wafer to better understand cross-wafer process changes. Thus, to minimize the amount of wafer area dedicated to metrology, target sizes must be reduced, along with the effective measurement box size.

The measurement box size refers to the minimum area on the specimen where measurement results are stable and not affected by edge effects (e.g., due to optical diffraction wings) in optical metrology. Hence, the smaller the measurement box size, the smaller the area required for metrology targets. In the semiconductor industry, where wafer space allocated to metrology targets is limited (often, within the scribe line or even within die), the desired box size specification can be often very challenging, such as 30 μm×30 μm, 10 μm×10 μm, or even smaller.

In general, it is often desirable to configure metrology systems with multiple angles of incidence and several wavelength bands to improve measurement results. For example, metrology systems having multiple angles of incidence are described by U.S. Pat. No. 6,429,943 entitled "Critical dimension analysis with simultaneous multiple angle of incidence measurements," issued Aug. 6, 2002, to KLA-Tencor Corporation, the contents of which are incorporated by reference as if fully set forth herein. In another example, metrology systems having several wavelength bands are described by U.S. Pat. No. 7,061,614 entitled "Measurement system with separate optimized beam paths," issued Jun. 13, 2006, to KLA-Tencor Corporation, the contents of which are incorporated by reference as if fully set forth herein. However, in many examples, the use of multiple angles of incidence and multiple wavelength bands gives rise to geometric effects, diffraction, aberration, and other image quality effects that cause an undesirable enlargement of the measurement box size.

In some examples, measurement box size is reduced by minimizing spillover illumination light projected onto the measurement target outside of the measurement target area. In the past, the illumination spot size was reduced by increasing the system NA and reducing the size of the illumination aperture (e.g., a polarizer slit). Although increasing the NA addresses diffraction induced spillover, increasing the NA increases aberrations, increases cost, creates optical alignment difficulties, and reduces the transmission efficiency of the optical system. Although reducing the size of the illumination aperture addresses geometrical properties of the spot image, the reduction in size of the illumination aperture increases coherence effects, reduces light throughput, and requires a tightening of optical system tolerances.

In another example, large spot size illumination is used to illuminate the target and spillover light illuminates structures outside of the measurement target area. The collected signals are projected as an image onto a CCD image sensor. Only the signals associated with the measurement target are selected from the CCD image. Although, this may effectively reduce measurement box size for image based measurements, this approach cannot be used with spectroscopic signals.

It should also be noted that in some examples, a reduction in illumination spot size may not result in a reduced measurement box size. In particular, the interaction of illumination light with deep structures causes light to be scattered and reflected. This light, in turn, interacts with structures outside of the target area. In these examples, even if the illumination spot lands within the target area, the collected signals may still be contaminated from the light interactions with structures outside of the target area.

Despite existing approaches designed to control measurement box size, achieving a small measurement box size specification over the full measurement range is very challenging. This is especially the case at both large oblique angles of incidence (AOI), where the incident beam covers a larger area, and at longer wavelengths, where diffraction effects introduce significant limitations.

As lithographic and inspection systems are pressed to higher resolutions, measurement box size becomes a limiting factor in maintaining device yield. Thus, improved methods and systems for achieving a small effective measurement box size associated with a variety of metrology technologies are desired.

SUMMARY

Methods and systems for measuring metrology targets smaller than the illumination spot size employed to perform the measurement are described herein. Collected measurement signals contaminated with information from structures surrounding the target area are reconstructed to eliminate contributions from structures outside the target area. In one aspect, measurement signals associated with one or more small targets and one or more large targets located in close proximity to one another are used to train a signal reconstruction model. The model is subsequently used to reconstruct measurement signals from other small targets. In another aspect, multiple measurements of a small target at different locations within a target are de-convolved to estimate target area intensity. Reconstructed measurement signals are determined by a convolution of the illumination spot profile and the target area intensity.

In a further aspect, the reconstructed signals are used to estimate values of parameters of interest associated with the measured structures. For example, the reconstructed signals can be provided as measurement input to a physically based measurement model, a library based measurement model, a rigorous coupled wave analysis (RCWA) model, a signal response metrology (SRM) model, etc. In this manner, the reconstructed signals from the small targets can be used directly to measure structure and process parameters such as critical dimensions (CD), sidewall angle (SWA), height (HT), focus, dosage, and overlay.

In another further aspect, metrology target pairs including multiple small targets, multiple large targets, or both, located in proximity are employed to train the signal reconstruction model.

In another further aspect, multiple measurement techniques are employed to train the signal reconstruction model. In these examples, measurement signals associated with measurements of small targets, large targets, or both, by multiple measurement techniques are employed to train the signal reconstruction model.

In some examples, different metrology techniques are employed to generate measurement signals of one or more small targets and one or more large targets. In one example, SE measurements are performed on one or more large targets, but imaging scatterometry is employed to measure corresponding small targets for training of the signal reconstruction model. Subsequently, the trained signal reconstruction model is used to reconstruct imaging scatterometry measurements of small targets to equivalent large target SE measurements.

In another further aspect, multiple measurement instances of one or more small targets, one or more large targets, or both are employed to train the signal reconstruction model. The multiple measurement instances each involve different values of one or more measurement system parameters. Exemplary measurement system parameters include illumination wavelength, azimuth angle, angle of incidence, polarization state, depth of focus, and measurement location within each metrology target.

In another further aspect, a signal reconstruction model is trained based on metrology pairs having one or more metrology targets, one or more measurement systems, one or more measurement system configurations, or any combination thereof.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

BRIEF DESCRIPTION OF THE DRAWINGS

FIG. 10 depicts vector 190 of measurement signals associated with M different large metrology targets, each measured by N different measurement systems or measurement system configurations.

DETAILED DESCRIPTION

Reference will now be made in detail to background examples and some embodiments of the invention, examples of which are illustrated in the accompanying drawings.

Methods and systems for measuring metrology targets smaller than the illumination spot size employed to perform the measurement are described herein. Valuable wafer area is saved by reducing the size of metrology targets.

Measurement signals are collected from small size metrology targets by a metrology system with an illumination spot larger than the metrology target. The illumination light effectively overfills the metrology target. The collected measurement signals are contaminated with signal information from structures surrounding the target. The contaminated measurement signals are reconstructed to eliminate signal information associated with surrounding structures from the contaminated measurement signals. The resulting reconstructed signals only include signal information associated with the structure under measurement.

Figure 1:
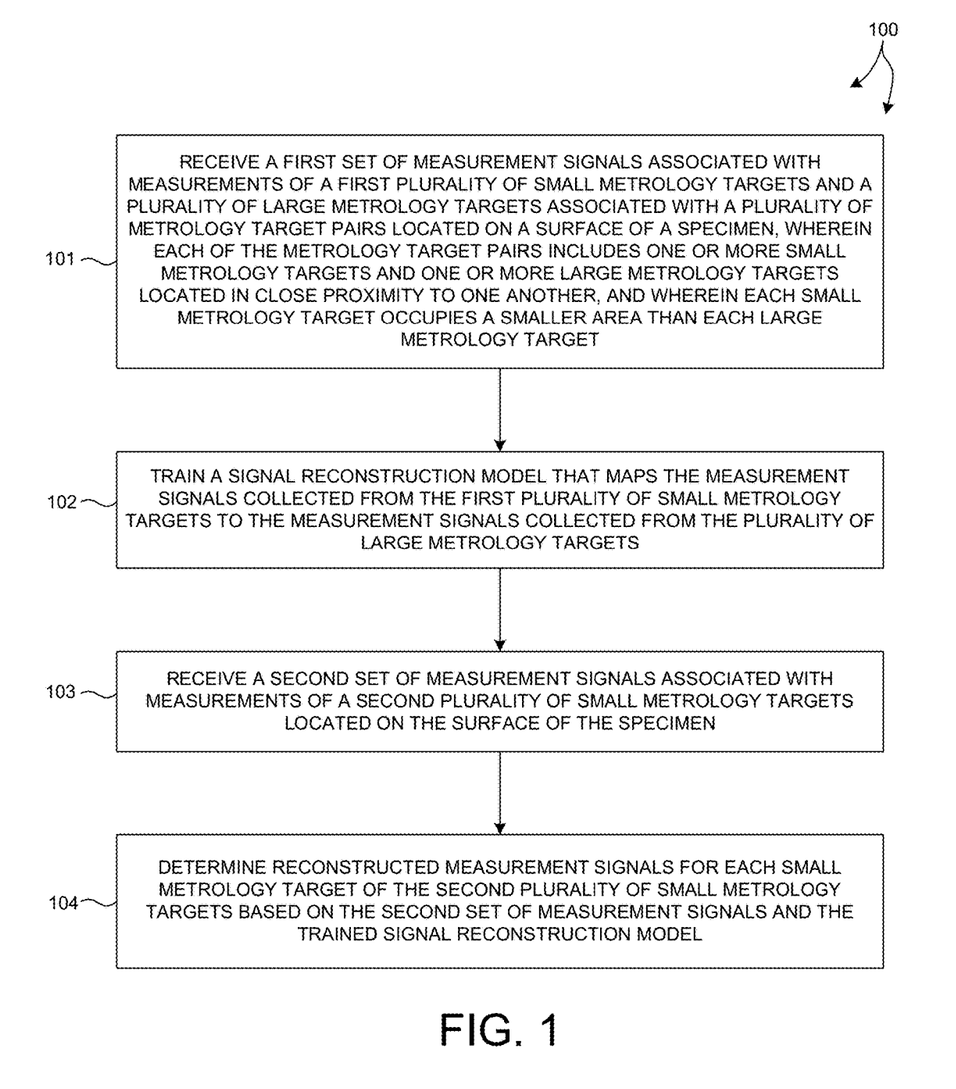
FIG. 1 is a flowchart illustrative of a method 100 of reducing the effective measurement box size of a metrology system as described herein.

FIG. 1 illustrates an exemplary method 100 for reducing the effective measurement box size of a metrology system. Method 100 is suitable for implementation by a metrology system such as metrology system 300 illustrated in FIG. 12 of the present invention. In one aspect, it is recognized that data processing blocks of method 100 may be carried out via a pre-programmed algorithm executed by one or more processors of computing system 330, or any other general purpose computing system. It is recognized herein that the particular structural aspects of metrology system 300 do not represent limitations and should be interpreted as illustrative only.

In block 101, a set of measurement signals are received, e.g., by computing system 330. The measurement signals are associated with measurements of small metrology targets and large metrology targets that make up a number of metrology target pairs located across the surface of specimen. Each of the metrology target pairs includes one or more small metrology targets and one or more large metrology targets located in close proximity to one another. Each small metrology target occupies a smaller area than each large metrology target. The illumination spot size of the measurement system exceeds the size of each small metrology target. In some embodiments, at least one of the large metrology targets includes the same structures as at least one of the small metrology targets.

Figure 2:
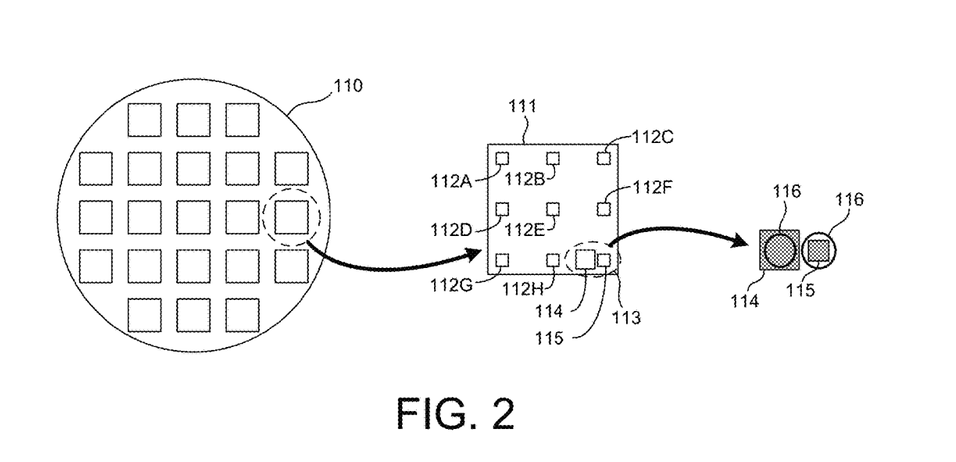
FIG. 2 depicts a wafer 110 including multiple fields. Each field includes multiple small targets distributed across each field and at least one metrology target pair.

FIG. 2 depicts a wafer 110 including multiple fields such as field 111. Each field includes multiple small targets distributed across the field and at least one metrology target pair. A metrology target pair includes a small target and a large target located in close proximity (e.g., adjacent to one another). The small targets are smaller than the illumination spot of the measurement system employed to perform the measurements. Thus, the small targets are overfilled. The large target is larger than the illumination spot of the measurement system employed to perform the measurements. Thus, the large targets are underfilled. It is noted that the term "overfilled" corresponds to any type of influence on the measured signal by the region outside of the metrology target or targets. This may occur even in situations when the actual illumination spot is smaller than the target. For example even when the actual illumination spot is smaller than the target, imperfect alignment of the beam with the metrology target may still result in signal contamination.

As depicted in FIG. 2, field 111 includes targets 112A-H and target 115. In addition, field 111 includes a large target 114. Small target 115 and large target 114 are located in close proximity to one another and together form a metrology target pair 113. Also as depicted in FIG. 2, illumination spot 116 overfills small target 115 and underfills large target 114. In some examples, small metrology target 115 is a 10 micrometer by 10 micrometer box target, and large metrology target 114 is a 30 micrometer by 30 micrometer box target. These dimensions are provided by way of non-limiting example. Any other suitable dimensions may be contemplated within the scope of this patent document.

In block 102, a signal reconstruction model is trained to map the measurement signals collected from the small metrology targets of the metrology target pairs to the measurement signals collected from the large metrology targets of the metrology target pairs. In some embodiments, metrology target pairs from the same wafer are used to train the signal reconstruction model. However, in general, measurement signals from metrology target pairs from multiple wafers may be employed to train the signal reconstruction model. A trained signal reconstruction model predicts uncontaminated (i.e., large target) signals from contaminated (i.e., small target) signals.

In one example, the signal reconstruction model is a linear model employing a linear combination of principal components. As illustrated in equation (1), a linear model pairs k principal components of small targets, $PC_{Small}$, with large target signals, $S_{Large}$. $\alpha(i)$ represents linear parameter values associated with each principal component and $\epsilon$ is a fitting noise parameter.

$$S_{Large} = \sum_{i=0}^{k} \alpha(i) \cdot PC_{Small}(i) + \epsilon \quad (1)$$

The linear model of equation (1) is provided by way of non-limiting example. Many other linear and nonlinear functions may be contemplated to map the measurement signals collected from the small metrology targets of the metrology target pairs to the measurement signals collected from the large metrology targets of the metrology target pairs. For example, the signal reconstruction model may be a neural network model or a support vector machine model, etc.

In block 103, a set of measurement signals associated with measurements of other small metrology targets located on the surface of the specimen are received, e.g., by computing system 330.

In general, at least some, if not all of the measurement signals received in block 103 are associated with small metrology targets that did not participate in the training of the signal reconstruction model. As depicted in FIG. 2, small metrology targets 112A-H are not part of metrology pair 113. In one example, measurement signals associated with these small targets are received in block 103.

In block 104, reconstructed measurement signals are determined for each small metrology target for which measurement signals were received in block 103. The reconstructed measurement signals are determined based on the received measurement signals and the trained signal reconstruction model. Equation (2) illustrates the trained signal reconstruction model of equation (1) applied to principal components of the measurement signals received in block 103. $\alpha(i)$ represents the linear parameter values illustrated in FIG. 2, $PC_{Small}$ represents the principal components of the measurement signals associated with the small metrology targets received in block 103, and $S_{Reconstructed}$ represents the reconstructed measurement signals associated with each of the small metrology targets for which measurement signals were received in block 103.

$$S_{Reconstructed} = \sum_{i=0}^{k} \alpha(i) \cdot PC_{Small}(i) \quad (2)$$

The reconstructed measurement signals are stored in a memory (e.g., memory 332).

In a further aspect, the reconstructed signals are used to estimate values of parameters of interest using any known measurement technique. For example, the reconstructed signals can be provided as measurement input to a physically based measurement model, a library based measurement model, a rigorous coupled wave analysis (RCWA) model, a signal response metrology (SRM) model, etc.

In some examples, the reconstructed measurement signals are used for both training of a SRM model and measurement using the trained SRM model. In one example, optical critical dimension (OCD) measurements of large metrology targets are performed to determine values of one or more parameters of interest. This measurement data, along with reconstructed measurement signals associated with corresponding small targets is used to train a SRM measurement model. The trained SRM model is subsequently used to estimate values of parameters of interest based on reconstructed signals from small metrology targets. In this manner, the reconstructed signals from the small targets can be used directly for measuring structure and process parameters such as CD, SWA, HT, Focus, Dose, Overlay.

SRM model training and measurements are described in further detail in U.S. Patent Publication No. 2014/0297211, U.S. Patent Publication No. 2014/0316730, and U.S. Patent Publication No. 2015/0046118, the subject matter of each are incorporated herein by reference in their entirety.

Figure 3:
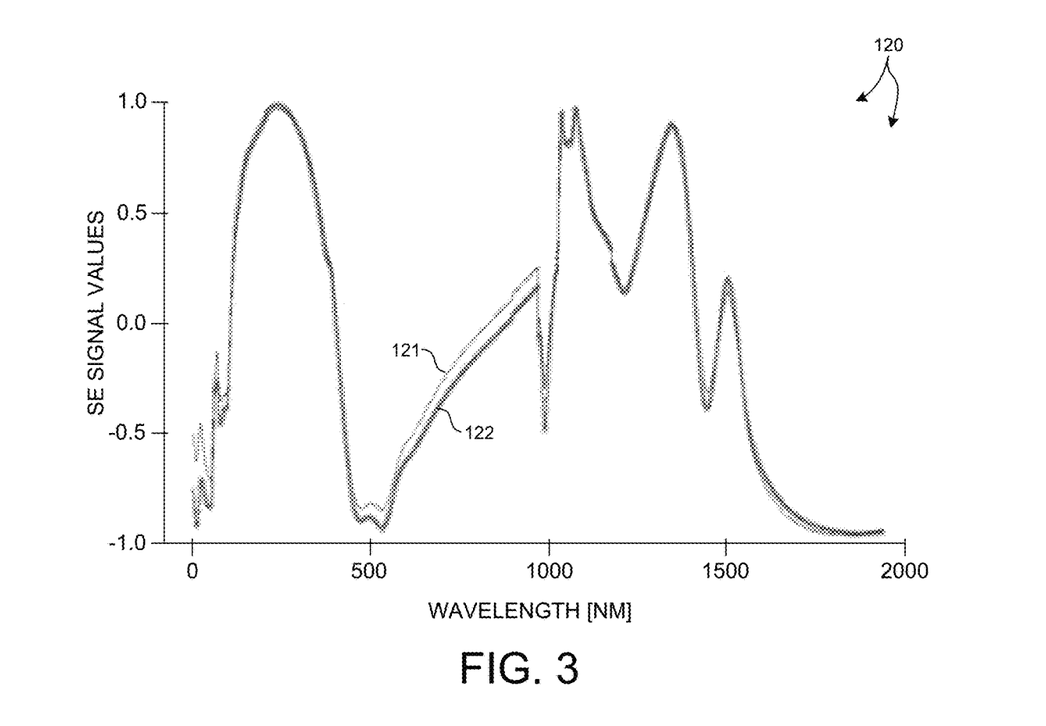
FIG. 3 depicts a plot 120 of spectroscopic ellipsometry (SE) signals 121 contaminated with information from structures outside the target area and SE signals 122 that are reconstructed from SE signals 121.

FIG. 3 depicts a plot 120 of spectroscopic ellipsometry (SE) signals 121 collected from 10 micrometer targets. As described hereinbefore, SE signals 121 are contaminated with information from structures outside the target area because the SE illumination spot overfills the 10 micrometer by 10 micrometer targets. In addition plot 120 illustrates reconstructed SE signals 122 that are reconstructed from SE signals 121. The reconstructed signals 122 overlay almost perfectly with the uncontaminated SE signals collected from 30 micrometer targets (not shown). The SE signals collected from the 30 micrometer by 30 micrometer targets are not contaminated with information from structures outside the target area because the SE illumination spot underfills the 30 micrometer by 30 micrometer targets. The correction introduced by the signal reconstruction model is visible in the differences between reconstructed SE signals 122 and contaminated SE signals 121.

In a further aspect, multiple small targets, multiple large targets, or both are employed to train the signal reconstruction model.

Figure 4:
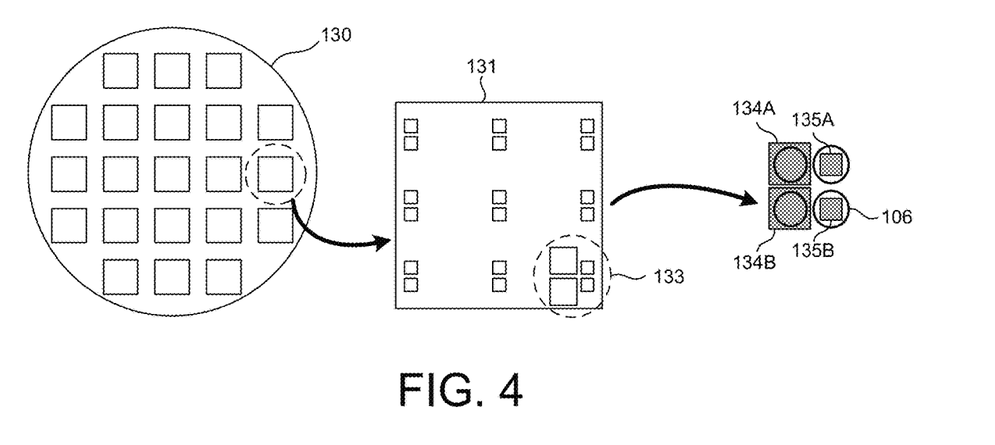
FIG. 4 depicts a wafer 130 including multiple fields. Each field includes two small targets 135A and 135B and two large targets 134A and 134B located in close proximity.

FIG. 4 depicts a wafer 130 including multiple fields such as field 131. Each field includes multiple small targets distributed across the field and metrology target pair 133. Metrology target pair 133 includes two small targets 135A and 135B and two large targets 134A and 134B located in close proximity (e.g., adjacent to one another). The small targets are smaller than the illumination spot 106 of the measurement system employed to perform the measurements. Thus, the small targets are overfilled. The large target is larger than the illumination spot 106 of the measurement system employed to perform the measurements. Thus, the large targets are underfilled. Wafer 130 and field 131 are depicted by way of non-limiting example. In general, metrology target pairs employed to train a signal reconstruction model as described herein may include any suitable number of large targets and any suitable number of small targets.

In one example, it may be desirable to measure two or more 10 micrometer by 10 micrometer targets placed next to one another. This is desirable in the metrology of lithography processes where isolated and dense targets are often used for focus, dose, and critical dimension metrology. This is also desirable in overlay metrology where multiple targets with known overlay offset are commonly employed. In these examples, two or more targets are illuminated. The collected signals contain information about these targets as well as undesired information due light interaction with areas between and around the targets as well as diffracted field interference among the separate targets.

Figure 5:
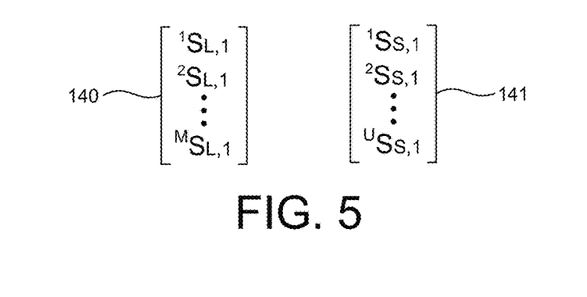
FIG. 5 depicts vector 140 of measurement signals associated with large targets and vector 141 of measurement signals associated with measurement signals of small targets.

Method 100 is applied as described hereinbefore to train a signal reconstruction model that maps signals from multiple small targets to measurement signals from multiple large targets spaced far enough apart to prevent undesired interactions. FIG. 5 depicts vector 140 of measurement signals associated with large targets {1,M} for a particular measurement instance, where M is any suitable integer number. FIG. 5 also depicts vector 141 of measurement signals associated with small targets {1,U} for a particular measurement instance, where U is any suitable integer number. These vectors of measurement signals may be applied to equations (1) and (2), or more generally as described with reference to method 100 to train a signal reconstruction model and reconstruct small target signals based on measurements of any number of small and large targets. Multiple targets may be employed advantageously to save wafer area, access more structural degrees of freedom, break correlations, and improve throughput.

In another further aspect, multiple measurement techniques are employed to train the signal reconstruction model. In some examples, multiple metrology techniques are employed to generate measurement signals of one or more small targets, one or more large targets, or both. In these examples, measurement signals associated with measurements of small targets, large targets, or both, by multiple measurement techniques are employed to train the signal reconstruction model.

In some examples, different metrology techniques are employed to generate measurement signals of one or more small targets and one or more large targets. In one example, SE measurements are performed on one or more large targets, but imaging scatterometry is employed to measure corresponding small targets for training of the signal reconstruction model. Subsequently, the trained signal reconstruction model is used to reconstruct imaging scatterometry measurements of small targets to equivalent large target SE measurements.

In some examples, contaminated measurement signals measured by one metrology technique are reconstructed to generate measurement signals of a small box size metrology target by another metrology technique without contamination by surrounding structures. In this manner, one type of signal is reconstructed from another type of signal. Exemplary signal types include extreme ultraviolet spectroscopic reflectometry, SE, two-dimensional beam profile reflectometry, small-angle x-ray scatterometry, x-ray diffraction, raman imaging, atomic force microscopy, scanning electron microscopy, tunneling electron microscopy, etc.

In another further aspect, multiple measurement instances of one or more small targets, one or more large targets, or both are employed to train the signal reconstruction model. The multiple measurement instances each involve different values of one or more measurement system parameters. Exemplary measurement system parameters include illumination wavelength, azimuth angle, angle of incidence, polarization state, depth of focus, and measurement location within each metrology target.

Figure 6:
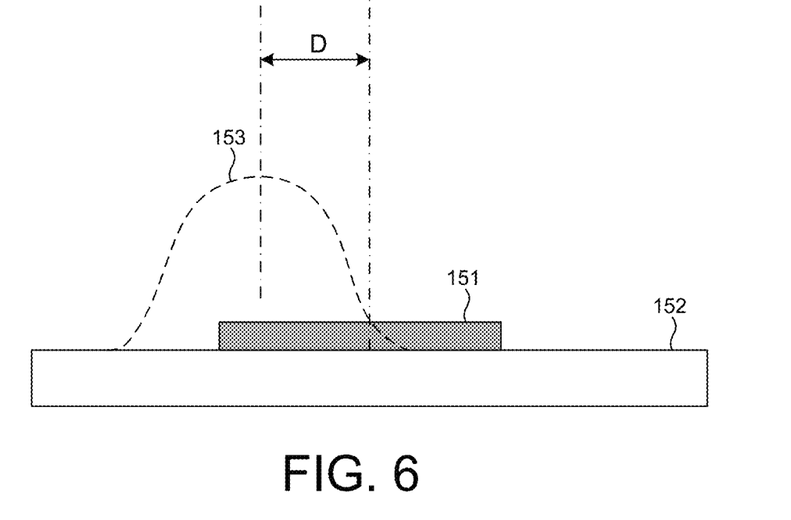
FIG. 6 depicts metrology target 151 illuminated with light having an illumination profile 153 that is offset from the center of the metrology target.
Figure 7:
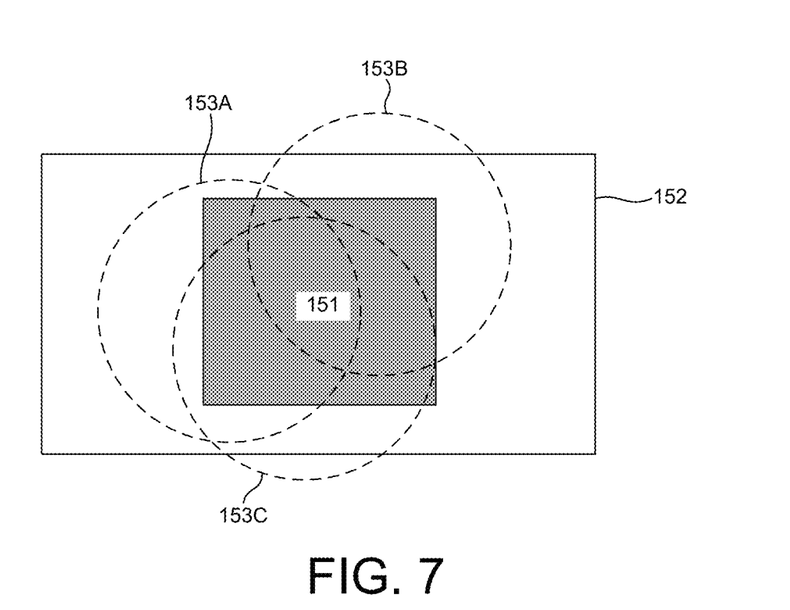
FIG. 7 depicts a top view of the same metrology target 151. In this view, the center of illumination profile 153 is depicted in three different locations 153A-C within the area of metrology target 151.

In some examples, measurement signals from measurements of one or more small targets, one or more large targets, or both, at different locations within each metrology target are generated. These measurement signals are employed to train the signal reconstruction model as described with reference to method 100. In these examples, the same target is measured at multiple positions. For each position, the beam covers different portions of the target area and its surrounding area. FIG. 6 depicts metrology target 151 disposed on specimen 152. Illumination profile 153 is offset from the center of metrology target 151 by a distance, D. FIG. 7 depicts a top view of the same metrology target 151. In this view, the center of illumination profile 153 is depicted in three different locations 153A-C within the area of metrology target 151. In this example, measurement signals generated for each illumination location are employed to train the signal reconstruction model.

Figure 8:
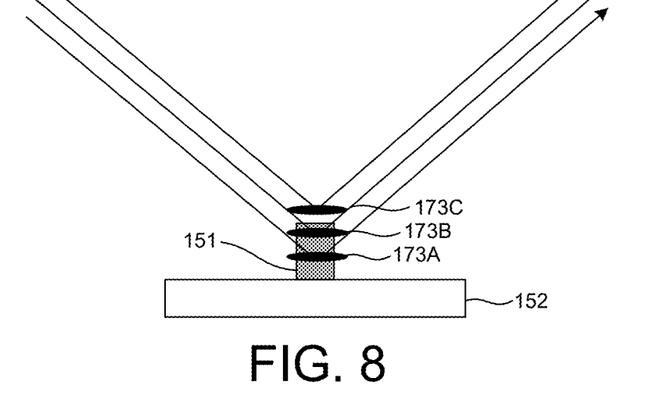
FIG. 8 depicts metrology target 151 disposed on specimen 152. Illumination is focused at three different offset distances from the surface of specimen 152.

In some other examples, measurement signals from measurements of one or more small targets, one or more large targets, or both, at different focus offsets are generated. These measurement signals are employed to train the signal reconstruction model as described with reference to method 100. FIG. 8 depicts metrology target 151 disposed on specimen 152. Illumination spots 173A-C are focused at three different offset distances from the surface of specimen 152. In this example, measurement signals generated for each focus offset are employed to train the signal reconstruction model.

In some examples, measurement signals measured at one measurement system configuration are reconstructed to generate measurement signals at another measurement system configuration without contamination by surrounding structures. For example, signals with a specific set of wavelengths and angles of incidence are reconstructed to signals with a different set of wavelengths and angles of incidence.

Figure 9:
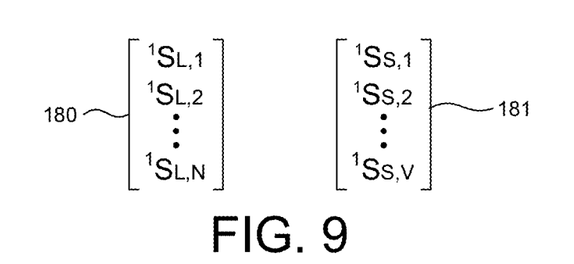
FIG. 9 depicts vector 180 of measurement signals associated with a large target and vector 181 of measurement signals associated with a small target.

In general, method 100 is applied as described hereinbefore to train a signal reconstruction model that maps signals from one or more small targets to measurement signals from one or more large targets measured by one or more different measurement systems, different measurement system configurations, or both. FIG. 9 depicts vector 180 of measurement signals associated with a large target by N different measurement system configurations of measurement system parameters, different measurement systems, or any combination, where N is any suitable integer number. FIG. 9 also depicts vector 181 of measurement signals associated with a small target by V different measurement system configurations of measurement system parameters, different measurement systems, or any combination, where V is any suitable integer number. These vectors of measurement signals may be applied to equations (1) and (2), or more generally as described with reference to method 100 to train a signal reconstruction model and reconstruct small target signals based on measurements of any number of small and large targets. Multiple measurement systems, multiple different measurement system settings, or both may be employed advantageously to save wafer area, access more structural degrees of freedom, break correlations, and improve throughput.

Figure 10:
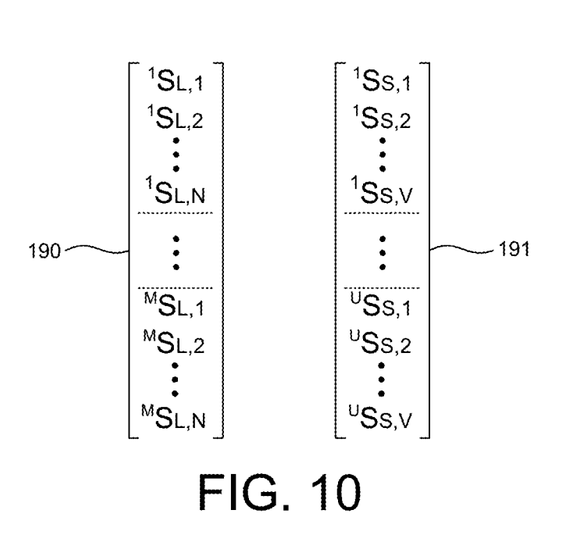
FIG. 10 also depicts vector 191 of measurement signals associated with U different small metrology targets, each measured by V different measurement systems or measurement system configurations.

In a further aspect, a signal reconstruction model is trained based on one or more metrology targets, one or more measurement systems, one or more measurement system configurations, or any combination thereof. FIG. 10 depicts vector 190 of measurement signals associated with M different large metrology targets, each measured by N different measurement systems or measurement system configurations. Similarly, FIG. 10 also depicts vector 191 of measurement signals associated with U different small metrology targets, each measured by V different measurement systems or measurement system configurations. These vectors of measurement signals may be applied to equations (1) and (2), or more generally as described with reference to method 100 to train a signal reconstruction model and reconstruct small target signals based on measurements of any combination of small and large targets by any combination of different measurement systems or measurement system configurations.

Figure 11:
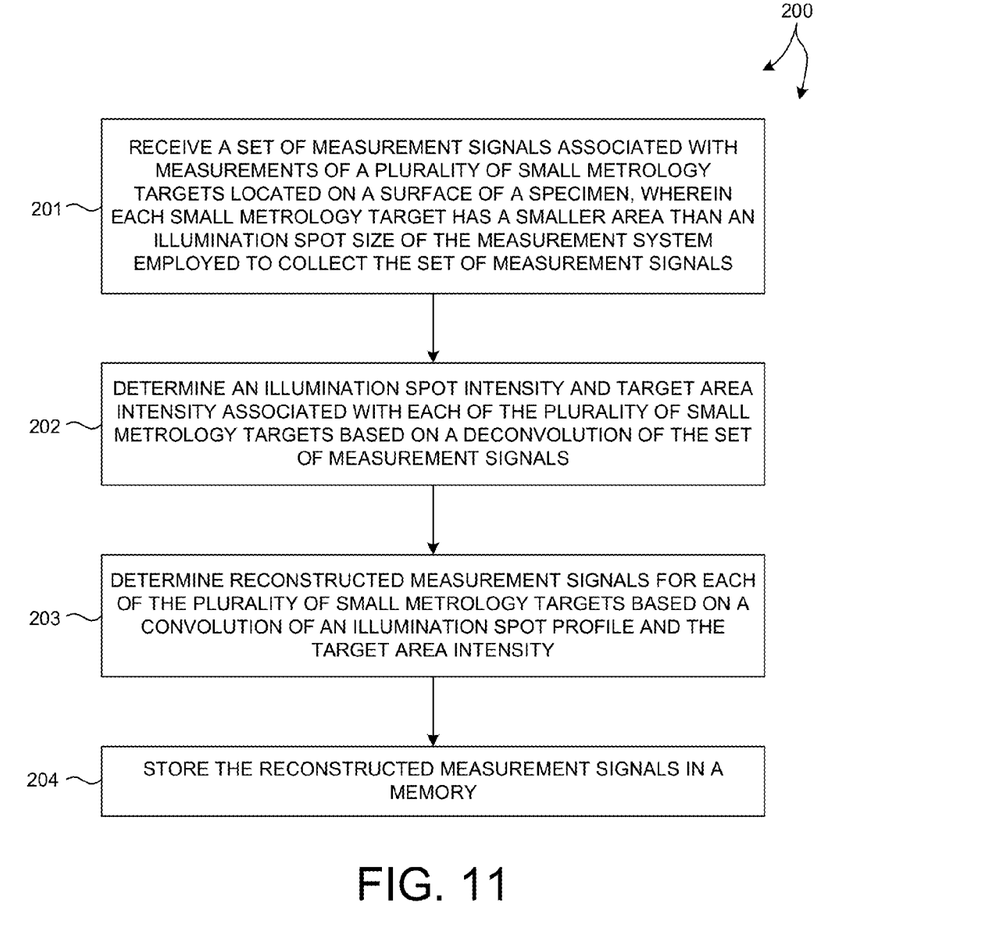
FIG. 11 illustrates a flowchart of another exemplary method 200 for reducing the effective measurement box size of a metrology system as described herein.

FIG. 11 illustrates another exemplary method 200 for reducing the effective measurement box size of a metrology system by reconstructing the measurement signal associated with the target structure from measurement signals contaminated by information from surrounding structures. Method 200 is suitable for implementation by a metrology system such as metrology system 300 illustrated in FIG. 12 of the present invention. In one aspect, it is recognized that data processing blocks of method 200 may be carried out via a pre-programmed algorithm executed by one or more processors of computing system 330, or any other general purpose computing system. It is recognized herein that the particular structural aspects of metrology system 300 do not represent limitations and should be interpreted as illustrative only.

In block 201, a set of measurement signals are received, e.g., by computing system 330. Measurement signals are collected from multiple samples at different locations within a small metrology target as depicted in FIGS. 6 and 7. The illumination spot overfills the target and the collected data contains contamination from outside the target area.

In block 202, an illumination spot intensity and target area intensity associated with each of the plurality of small metrology targets are determined based on a deconvolution of the set of measurement signals.

The Fourier transform of the contaminated signals, $S_{F,C}$, is related to the Fourier transform of the known illumination spot profile, $f_F(u,v)$ multiplied by Fourier transform of the unknown illumination spot intensity, $I_F(u,v)$ as illustrated in equation (3).

$$S_{F,C}(u,v) = f_F(u,v) \cdot I_F(u,v) \tag{3}$$

A deconvolution technique is applied to solve for the illumination spot intensity, $I(x,y)$ and the target area intensity, $T(x,y)$. Applicable deconvolution techniques include inverse filtering, pseudo-inverse filtering, and Wiener filtering.

Another deconvolution technique is a least squares estimate of an overdetermined system of equations. A least squares estimate provides a direct solution to an overdetermined system of linear equations assembled from all line scan positions. This approach also results in an estimate for the illumination spot intensity, $I(x,y)$ and the target area intensity, $T(x,y)$.

In block 203, reconstructed measurement signals are determined for each small metrology target for which measurement signals were received in block 201. The uncontaminated, reconstructed signals, $S_R$, are determined by the convolution of the illumination spot profile, $f(x,y)$ and the target area intensity, $T(x,y)$ as illustrated in equation (4)

$$S_R = f(x,y) \otimes T(x,y) \tag{4}$$

In a further aspect, the reconstructed signals are used to estimate values of parameters of interest using any known measurement technique as described hereinbefore. For example, the reconstructed signals can be provided as measurement input to a physically based measurement model, a library based measurement model, a rigorous coupled wave analysis (RCWA) model, a signal response metrology (SRM) model, etc.

In block 204, the reconstructed measurement signals are stored in a memory (e.g., memory 332).

In a further aspect, the reconstructed measurement signals determined in accordance with method 200 are provided as uncontaminated measurement signals of the calibration targets (i.e., large targets) for the training of a signal reconstruction model in accordance with method 100 as described hereinbefore.

In another further aspect, the signal reconstruction techniques described herein may be applied to suppress other unwanted signal contamination sources affecting metrology performance. In one example, some optical component imperfections make it difficult to achieve accurate tool-to-tool matching with traditional methods. In this example, calibration and system matching is achieved employing the methods described herein. The measurement signals associated with reference measurement targets (e.g., large targets) are provided by a reference tool. Signals associated with measurements of the reference targets by other tool(s) are collected and their measurement signals are "reconstructed" to suppress unwanted signal contamination relevant to these tools. In general, the signal reconstruction algorithm isolates the signal(s) associated with the metrology target and suppresses signal components associated with unwanted target areas or unwanted system-specific effects.

Figure 12:
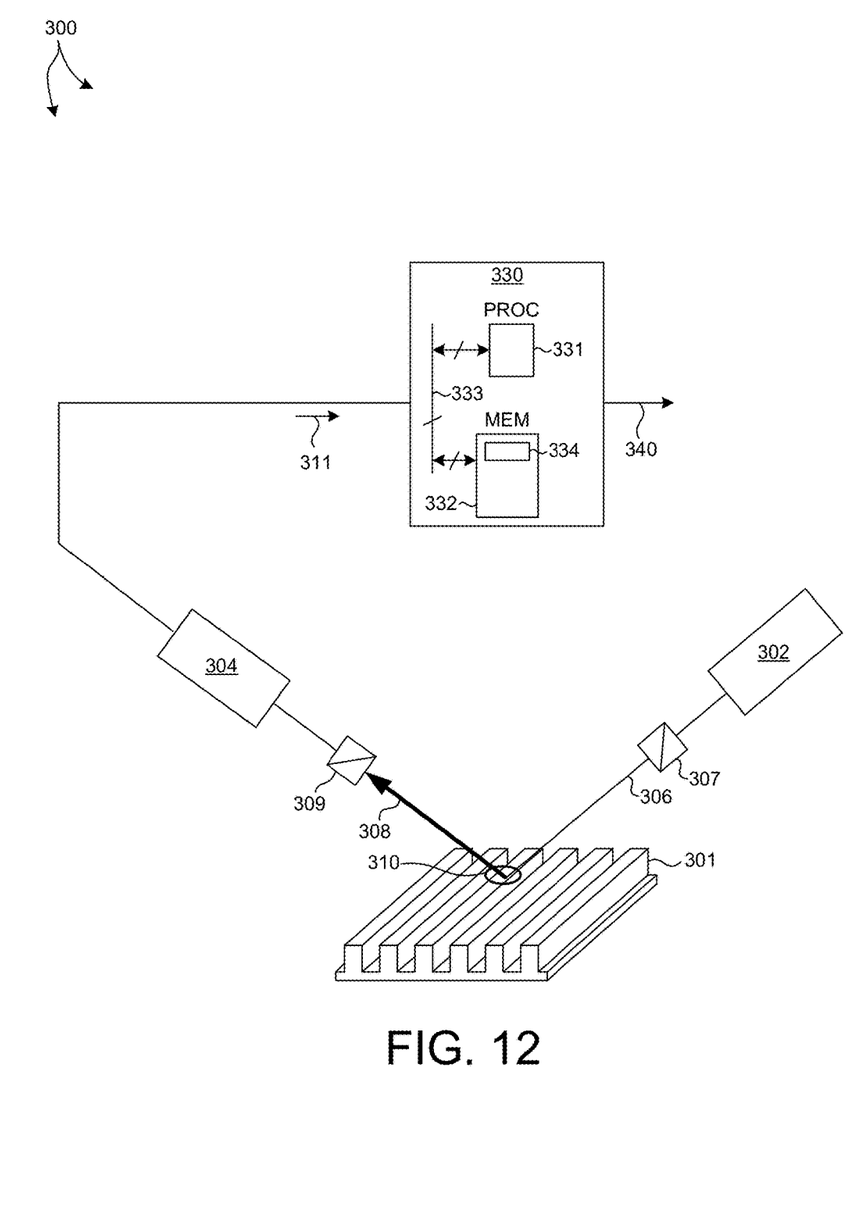
FIG. 12 illustrates a system 300 for reconstructing measurement signals in accordance with the exemplary methods presented herein.

FIG. 12 illustrates a system 300 for measuring characteristics of a specimen in accordance with the exemplary methods presented herein. As shown in FIG. 12, the system 300 may be used to perform spectroscopic ellipsometry measurements of one or more structures of a specimen 301. In this aspect, the system 300 may include a spectroscopic ellipsometer equipped with an illuminator 302 and a spectrometer 304. The illuminator 302 of the system 300 is configured to generate and direct illumination of a selected wavelength range (e.g., 150-850 nm) to the structure 310 disposed on the surface of the specimen 301. In turn, the spectrometer 304 is configured to receive illumination reflected from the surface of the specimen 301. It is further noted that the light emerging from the illuminator 302 is polarized using a polarization state generator 307 to produce a polarized illumination beam 306. The radiation reflected by the structure disposed on the specimen 301 is passed through a polarization state analyzer 309 and to the spectrometer 304. The radiation received by the spectrometer 304 in the collection beam 308 is analyzed with regard to polarization state, allowing for spectral analysis by the spectrometer of radiation passed by the analyzer. These spectra 311 are passed to the computing system 330 for analysis of the structure.

As depicted in FIG. 12, system 300 includes a single measurement technology (i.e., SE). However, in general, system 300 may include any number of different measurement technologies. By way of non-limiting example, system 300 may be configured as a spectroscopic ellipsometer (including Mueller matrix ellipsometry), a spectroscopic reflectometer, a spectroscopic scatterometer, an overlay scatterometer, an angular resolved beam profile reflectometer, a polarization resolved beam profile reflectometer, a beam profile reflectometer, a beam profile ellipsometer, any single or multiple wavelength ellipsometer, or any combination thereof. Furthermore, in general, measurement data collected by different measurement technologies and analyzed in accordance with the methods described herein may be collected from multiple tools, rather than one tool integrating multiple technologies.

In a further embodiment, system 300 may include one or more computing systems 330 employed to perform measurements based on measurement models developed in accordance with the methods described herein. The one or more computing systems 330 may be communicatively coupled to the spectrometer 304. In one aspect, the one or more computing systems 330 are configured to receive measurement data 311 associated with measurements of the structure of specimen 301.

It should be recognized that the various steps described throughout the present disclosure may be carried out by a single computer system 330 or, alternatively, a multiple computer system 330. Moreover, different subsystems of the system 300, such as the spectroscopic ellipsometer 304, may include a computer system suitable for carrying out at least a portion of the steps described herein. Therefore, the aforementioned description should not be interpreted as a limitation on the present invention but merely an illustration. Further, the one or more computing systems 330 may be configured to perform any other step(s) of any of the method embodiments described herein.

In addition, the computer system 330 may be communicatively coupled to the spectrometer 304 in any manner known in the art. For example, the one or more computing systems 330 may be coupled to computing systems associated with the spectrometer 304. In another example, the spectrometer 304 may be controlled directly by a single computer system coupled to computer system 330.

The computer system 330 of the metrology system 300 may be configured to receive and/or acquire data or information from the subsystems of the system (e.g., spectrometer 304 and the like) by a transmission medium that may include wireline and/or wireless portions. In this manner, the transmission medium may serve as a data link between the computer system 330 and other subsystems of the system 300.

Computer system 330 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 330 and other systems (e.g., memory on-board metrology system 300, external memory, reference measurement tools, or other external systems). For example, the computing system 330 may be configured to receive measurement data from a storage medium (i.e., memory 332 or an external memory) via a data link. For instance, spectral results obtained using spectrometer 304 may be stored in a permanent or semi-permanent memory device (e.g., memory 332 or an external memory). In this regard, the spectral results may be imported from on-board memory or from an external memory system. Moreover, the computer system 330 may send data to other systems via a transmission medium. For instance, reconstructed measurement signals 340 determined by computer system 330 may be communicated and stored in an external memory. In this regard, measurement results may be exported to another system.

Computing system 330 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 334 implementing methods such as those described herein may be transmitted over a transmission medium such as a wire, cable, or wireless transmission link. For example, as illustrated in FIG. 12, program instructions 334 stored in memory 332 are transmitted to processor 331 over bus 333. Program instructions 334 are stored in a computer readable medium (e.g., memory 332). Exemplary computer-readable media include read-only memory, a random access memory, a magnetic or optical disk, or a magnetic tape.

In general, any measurement technique, or combination of two or more measurement techniques may be contemplated within the scope of this patent document. Exemplary measurement techniques include, but are not limited to spectroscopic ellipsometry, including Mueller matrix ellipsometry, spectroscopic reflectometry, spectroscopic scatterometry, scatterometry overlay, beam profile reflectometry, both angle-resolved and polarization-resolved, beam profile ellipsometry, single or multiple discrete wavelength ellipsometry, transmission small angle x-ray scatterometer (TSAXS), small angle x-ray scattering (SAXS), grazing incidence small angle x-ray scattering (GISAXS), wide angle x-ray scattering (WAXS), x-ray reflectivity (XRR), x-ray diffraction (XRD), grazing incidence x-ray diffraction (GIXRD), high resolution x-ray diffraction (HRXRD), x-ray photoelectron spectroscopy (XPS), x-ray fluorescence (XRF), grazing incidence x-ray fluorescence (GIXRF), low-energy electron induced x-ray emission scatterometry (LEXES), x-ray tomography, and x-ray ellipsometry. In general, any metrology technique applicable to the characterization of semiconductor structures, including image based metrology techniques, may be contemplated. Additional sensor options include electrical sensors such as non-contact capacitance/voltage or current/voltage sensors which bias the device and detect the resulting bias with an optical sensor (or the converse), or assisted optical techniques, such as XRD, XRF, XPS, LEXES, SAXS, and pump probe techniques. In one embodiment a two-dimensional beam profile reflectometer (pupil imager) may be used to collect both angle resolved and/or multi-spectral data in a small spot size. A UV Linnik interferometer may also be used as a Mueller matrix spectral pupil imager.

In some examples, the model building, training, and measurement methods described herein are implemented as an element of a SpectraShape® optical critical-dimension metrology system available from KLA-Tencor Corporation, Milpitas, Calif., USA. In this manner, the model is created and ready for use immediately after the measurements collected by the system.

In some other examples, the model building and training methods described herein are implemented off-line, for example, by a computing system implementing AcuShape® software available from KLA-Tencor Corporation, Milpitas, Calif., USA. The resulting, trained model may be incorporated as an element of an AcuShape® library that is accessible by a metrology system performing measurements.

In yet another aspect, the measurement results described herein can be used to provide active feedback to a process tool (e.g., lithography tool, etch tool, deposition tool, etc.). For example, values of the depth and focus parameters determined using the methods described herein can be communicated to a lithography tool to adjust the lithography system to achieve a desired output. In a similar way etch parameters (e.g., etch time, diffusivity, etc.) or deposition parameters (e.g., time, concentration, etc.) may be included in a measurement model to provide active feedback to etch tools or deposition tools, respectively.

In general, the systems and methods described herein can be implemented as part of off-line or on-tool measurement.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method comprising:
   providing illumination radiation to a first plurality of small metrology targets and a plurality of large metrology targets disposed on a specimen, the illumination radiation provided by an illumination source of a metrology tool, the illumination radiation projected onto the first plurality of small metrology targets and the plurality of large metrology targets with an illumination spot size, wherein one or more of the first plurality of small metrology targets and one or more of the large metrology targets are located in close proximity to one another, and wherein each of the first plurality of small metrology targets occupies a smaller area than each of the plurality of large metrology targets;
   detecting an amount of radiation from the first plurality of small metrology targets and the plurality of large metrology targets specimen in response to the illumination radiation, the amount of radiation detected by a detector of the metrology tool;
   generating a measured response associated with the first plurality of small metrology targets and the plurality of large metrology targets based on the detected amounts of radiation, the measured response comprising a first set of measurement signals;
   training a signal reconstruction model that maps the measurement signals generated from the measurements of the first plurality of small metrology targets to the measurement signals generated from the measurements of the plurality of large metrology targets;
   providing illumination radiation to a second plurality of small metrology targets disposed on the specimen, the illumination radiation provided by the illumination source of the metrology tool, the illumination radiation projected onto the second plurality of small metrology targets with the illumination spot size, wherein each of the second plurality of small metrology targets occupies a smaller area than each of the plurality of large metrology targets;
   detecting an amount of radiation from the second plurality of small metrology targets in response to the illumination radiation, the amount of radiation detected by the detector of the metrology tool;
   generating a measured response associated with the second plurality of small metrology targets based on the detected amounts of radiation, the measured response comprising a second set of measurement signals; and
   determining reconstructed measurement signals for each small metrology target of the second plurality of small metrology targets based on the second set of measurement signals and the trained signal reconstruction model.

2. The method of claim 1, further comprising:
   determining one or more parameter values associated with one or more parameters of interest for each of the second plurality of small metrology targets based on the reconstructed measurement signals.

3. The method of claim 2, wherein the determining the one or more parameter values involves a signal response metrology model or a physically based measurement model.

4. The method of claim 3, wherein the one or more parameters of interest include any of a critical dimension, a sidewall angle, a height, an overlay parameter, a focus parameter, and a dosage parameter.

5. The method of claim 1, wherein the measurement signals associated with any of the large metrology targets and the first and second plurality of small metrology targets includes measurement signals associated with multiple measurement instances each involving a different measurement technique.

6. The method of claim 1, wherein the measurement signals associated with any of the large metrology targets and the first and second plurality of small metrology targets includes measurement signals associated with multiple measurement instances each involving different values of one or more measurement system parameters.

7. The method of claim 6, wherein the measurement system parameters include illumination wavelength, azimuth angle, angle of incidence, polarization state, depth of focus, and measurement location within each metrology target.

8. The method of claim 1, wherein at least a portion of the measurement signals associated with the first and second plurality of small metrology targets are associated with a different measurement technique than at least a portion of the measurement signals associated with the plurality of large metrology targets.

9. The method of claim 1, wherein at least a portion of the measurement signals associated with the first and second plurality of small metrology targets are associated with measurements involving different values of one or more measurement system parameters than at least a portion of the measurement signals associated with the plurality of large metrology targets.

10. The method of claim 1, wherein an area of each of the first plurality of small metrology targets and each of the second plurality of small metrology targets is smaller than the illumination spot size, and wherein an area of each of the plurality of large metrology targets is larger than the illumination spot size.

11. The method of claim 1, wherein at least one of the plurality of large metrology targets includes the same structures as at least one of the first plurality of small metrology targets.

12. A measurement system comprising:
an illumination source configured to supply illumination light having an illumination spot size projected onto a surface of a specimen;
a detector configured to collect an amount light from a first plurality of small metrology targets, a second plurality of small metrology targets, and a plurality of large metrology targets illuminated by the illumination light, wherein one or more of the first plurality of small metrology targets and one or more large metrology targets are located in close proximity to one another, and wherein an area of each of the small metrology targets is smaller than the illumination spot size and an area of each of the large metrology targets is larger than the illumination spot size; and
a computing system configured to:
train a signal reconstruction model that maps the measurement signals collected from the first plurality of small metrology targets to the measurement signals collected from the plurality of large metrology targets; and
determine reconstructed measurement signals for each small metrology target of the second plurality of small metrology targets based on the measurement signals collected from the first plurality of small metrology targets and the trained signal reconstruction model.

13. The measurement system of claim 12, wherein the computing system is further configured to determine one or more values associated with one or more parameters of interest for each of the second plurality of small metrology targets based on the reconstructed measurement signals.

14. The measurement system of claim 12, wherein the measurement signals associated with any of the large metrology targets and the first and second plurality of small metrology targets includes measurement signals associated with multiple measurement instances each involving a different measurement technique.

15. The measurement system of claim 12, wherein the measurement signals associated with any of the large metrology targets and the first and second plurality of small metrology targets includes measurement signals associated with multiple measurement instances each involving different values of one or more measurement system parameters.

16. The measurement system of claim 15, wherein the measurement system parameters include illumination wavelength, azimuth angle, angle of incidence, polarization state, depth of focus, and measurement location within each metrology target.

17. The measurement system of claim 12, wherein at least a portion of the measurement signals associated with the first and second plurality of small metrology targets are associated with a different measurement technique than at least a portion of the measurement signals associated with the plurality of large metrology targets.

18. The measurement system of claim 12, wherein at least a portion of the measurement signals associated with the first and second plurality of small metrology targets are associated with measurements involving different values of one or more measurement system parameters than at least a portion of the measurement signals associated with the plurality of large metrology targets.

19. A method comprising:
providing illumination radiation to a plurality of small metrology targets disposed on a specimen, the illumination radiation provided by an illumination source of a metrology tool, the illumination radiation projected onto the first plurality of small metrology targets with an illumination spot size, wherein each of the first plurality of small metrology targets occupies a smaller area than the illumination spot size;
detecting an amount of radiation from the plurality of small metrology targets in response to the illumination radiation, the amount of radiation detected by a detector of the metrology tool;
generating a measured response associated with the plurality of small metrology targets based on the detected amounts of radiation, the measured response comprising a set of measurement signals;
determining an illumination spot intensity and target area intensity associated with each of the plurality of small metrology targets based on a deconvolution of the set of measurement signals;
determining reconstructed measurement signals for each of the plurality of small metrology targets based on a convolution of an illumination spot profile and the target area intensity; and
storing the reconstructed measurement signals in a memory.

20. The method of claim 19, further comprising:
determining one or more parameter values associated with one or more parameters of interest for each of the plurality of small metrology targets based on the reconstructed measurement signals.

* * * * *